United States Patent
Gamache

(12) 
(10) Patent No.: US 6,645,994 B1
(45) Date of Patent: Nov. 11, 2003

(54) METHOD OF TREATING DRY EYE DISORDERS

(75) Inventor: Daniel A. Gamache, Arlington, TX (US)

(73) Assignee: Alcon, Inc., Hunenberg (CH)

( * ) Notice: Subject to any disclaimer, the term of this patent is extended or adjusted under 35 U.S.C. 154(b) by 0 days.

(21) Appl. No.: 10/152,142

(22) Filed: May 21, 2002

Related U.S. Application Data

(60) Provisional application No. 60/295,396, filed on Jun. 1, 2001.

(51) Int. Cl.$^7$ ............................................. A61K 31/425

(52) U.S. Cl. ...................................... 514/383; 514/912

(58) Field of Search .................................. 514/383, 912

(56) References Cited

U.S. PATENT DOCUMENTS

| | | | |
|---|---|---|---|
| 3,991,759 A | 11/1976 | Urquhart | 128/260 |
| 4,131,651 A | 12/1978 | Shah et al. | 424/78 |
| 4,370,325 A | 1/1983 | Packman | 424/245 |
| 4,409,205 A | 10/1983 | Shively | 424/78 |
| 4,744,980 A | 5/1988 | Holly | 424/78 |
| 4,804,539 A | 2/1989 | Guo et al. | 424/450 |
| 4,818,537 A | 4/1989 | Guo | 424/427 |
| 4,883,658 A | 11/1989 | Holly | 424/80 |
| 4,914,088 A | 4/1990 | Glonek et al. | 514/76 |
| 4,966,773 A | 10/1990 | Gressel et al. | 424/489 |
| 5,041,434 A | 8/1991 | Lubkin | 514/182 |
| 5,075,104 A | 12/1991 | Gressel et al. | 424/78.04 |
| 5,174,988 A | 12/1992 | Mautone et al. | 424/45 |
| 5,278,151 A | 1/1994 | Korb et al. | 514/76 |
| 5,290,572 A | 3/1994 | MacKeen | 424/602 |
| 5,294,607 A | 3/1994 | Glonek et al. | 514/76 |
| 5,371,108 A | 12/1994 | Korb et al. | 514/762 |
| 5,403,841 A | 4/1995 | Lang et al. | 514/226.8 |
| 5,578,586 A | 11/1996 | Glonek et al. | 514/76 |
| 5,620,921 A | 4/1997 | Sullivan | 514/178 |
| 5,677,335 A | 10/1997 | Robertson et al. | 514/521 |
| 5,696,166 A | 12/1997 | Yanni et al. | 514/573 |
| 5,800,807 A | 9/1998 | Hu et al. | 424/78.01 |
| 5,958,912 A | 9/1999 | Sullivan | 514/177 |
| 6,071,904 A | 6/2000 | Ali et al. | 514/222.8 |
| 6,096,733 A | 8/2000 | Lubkin | 514/182 |
| 6,107,289 A | 8/2000 | Sullivan | 514/178 |
| 6,153,607 A | 11/2000 | Pflugfelder et al. | 514/178 |

FOREIGN PATENT DOCUMENTS

| | | |
|---|---|---|
| WO | WO 95/31211 | 11/1995 |
| WO | WO 96/32105 | 10/1996 |
| WO | WO 00/03705 | 1/2000 |
| WO | WO 00/43000 | 7/2000 |
| WO | WO 00/61168 | 10/2000 |
| WO | WO 00/64863 | 11/2000 |
| WO | WO 01/64220 | 9/2001 |

OTHER PUBLICATIONS

Corey et al., Total Synthesis and Biological Activity of Lactacystin, Omuralide and Analogs, *Chem. Pharm. Bull.*, vol. 47, pp. 1–10 (1999).

Gamache eta l., "Preservation of Corneal Integrity by the Mucin Secretagogue 15(S)–HETE in a Rabbit Model of Desiccation–Induced Dry Eye," Cornea, vol. 19(2), pp. S88 (2000).

Jumblatt et al, "Effects of 15(S)–HETE on Human Conjunctival Mucin Secretion," Cornea, vol. 19(2), pp. S97 (2000).

Jumblatt et al., "Mucin Gene Expression in Human Conjunctiva," *IOVS*, vol. 36(4), pp. S997 (1995).

Jumblatt et al., "MUC5 is Synthesized and Secreted by Conjunctival Tissue," *IOVS*, vol. 38(4), pp. S466 (1997).

Jumblatt et al. "MUC5AC Mucin is a Component of the Human Precorneal Tear Film," *Invest. Oph & Vis. Science*, vol. 40(1), pp. 43–49 (1999).

Jumblatt et al., "Mucins of the Ocular Surface," *Cornea*, vol. 19(2), pp. S97 (2000).

Jumblatt et al., "Regulation of Mucin Secretion by P2Y2 Receptors in Conjunctival Goblet Cells," IOVS, vol. 39(4), pp. S803 (1998).

Jumblatt et al., "Regulation of Ocular Mucin Secretion by P2Y2 Nucleotide Receptors in Rabbit and Human Conjunctiva," Exp. Eye Res., vol. 67, pp. 341–346 (1998).

Lemp, "Report of the National Eye Institute/Industry Workshop on Clinical Trials in Dry Eyes," CLAO Journal, vol. 21(4), pp. 221–231 (1995).

McCulley et al., "Tear Film Structure and Dry Eye," Contactologia vol. 20, pp. 145–149 (1998).

McKenzie et al., "Quantification of MUC2 and MUC5AC Transcripts in Human Conjunctiva," *Investigative Ophthalmology & Vis. Science*, vol. 41(3), pp. 703–708 (2000).

McKenzie et al., "Relative Levels of MUC2 and MUC5AC in Human Conjunctiva," *IOVS*, vol. 39(4), pp. S535 (1998).

Marsh et al., "Topical Nonpreserved Methylprednisolone Therapy for Keratoconjunctivitis Sicca in Sjogren Syndrome," Ophthalmology, vol. 106(4), pp. 811–816 (1999).

Rolando et al., "Topical Non–Preserved 0.1% Diclofenac Therapy for Kerato–conjunctivitis Sicca," Cornea, vol. 19(2), p. S117 (2000).

Shine et al., "Keratoconjunctivitis Sicca Associated with Meibomian Secretion Polar Lipid Abnormality," Arch. Ophthalmol. vol. 116, pp. 849–852 (1998).

(List continued on next page.)

*Primary Examiner*—Zohreh Fay
(74) *Attorney, Agent, or Firm*—Patrick M. Ryan

(57) ABSTRACT

Inhibitors of acyl-CoA synthetase are useful for treating dry eye disorders and other disorders requiring the wetting of the eye.

6 Claims, No Drawings

OTHER PUBLICATIONS

Soucy et al., "A Novel and Efficient Synthesis of a Highly Active Analogue of clasto–Lactacystin β–Lactone," J. Am. Chem. Soc, vol. 121, pp. 9967–9976 (1999).

Tauber et al., "A Dose–Ranging Clinical Trial to Assess the Safety and Efficacy of Cyclosporine Ophthalmic Emulsion in Patients with Keratoconjunctivitis Sicca," Lacrimal Gland, Tear Film and Dry Eye Syndromes 2, edited by Sullivan et al., Plenum Press, New York, pp. 969–972 (1998).

Ubels et al., "The Eicosanoid, 15(S)–HETE, Stimulates Secretion of Mucin–Like Glycoprotein by the Corneal Epithelium," Cornea, vol. 19(2), p. S135 (2000).

Zhao et al., "Quantification of MUC5AC Protein in Human Tears," IOVS, vol. 39(4), p. S534 (1998).

Triacsin C Product Information, Kitasato Institute, May 12, 1998 (summary + 4 pages).

Triacsin C Product Information, Kamiya Biomedical Company, Jun. 1, 2001 (1 page).

METHOD OF TREATING DRY EYE DISORDERS

This application claims priority to U.S. Provisional Application, Serial No. 60/295,396, filed Jun. 1, 2001.

The present invention is directed to the treatment of dry eye disorders. In particular, the present invention is directed toward the use of inhibitors of acyl-CoA synthetase to treat dry eye and other disorders requiring the wetting of the eye in mammals.

BACKGROUND OF THE INVENTION

Dry eye, also known generically as *keratoconjunctivitis sicca*, is a common ophthalmological disorder affecting millions of Americans each year. The condition is particularly widespread among post-menopausal women due to hormonal changes following the cessation of fertility. Dry eye may afflict an individual with varying severity. In mild cases, a patient may experience burning, a feeling of dryness, and persistent irritation such as is often caused by small bodies lodging between the eye lid and the eye surface. In severe cases, vision may be substantially impaired. Other diseases, such as Sjogren's disease and cicatricial pemphigoid manifest dry eye complications.

Although it appears that dry eye may result from a number of unrelated pathogenic causes, all presentations of the complication share a common effect, that is the breakdown of the pre-ocular tear film, which results in dehydration of the exposed outer surface and many of the symptoms outlined above (Lemp, Report of the National Eye Institute/Industry Workshop on Clinical Trials in Dry Eyes, *The CLAO Journal*, volume 21, number 4, pages 221–231 (1995)).

Practitioners have taken several approaches to the treatment of dry eye. One common approach has been to supplement and stabilize the ocular tear film using so-called artificial tears instilled throughout the day. Other approaches include the use of ocular inserts that provide a tear substitute or stimulation of endogenous tear production.

Examples of the tear substitution approach include the use of buffered, isotonic saline solutions, aqueous solutions containing water soluble polymers that render the solutions more viscous and thus less easily shed by the eye. Tear reconstitution is also attempted by providing one or more components of the tear film such as phospholipids and oils. Phospholipid compositions have been shown to be useful in treating dry eye; see, e.g., McCulley and Shine, Tear film structure and dry eye, *Contactologia*, volume 20(4), pages 14549 (1998); and Shine and McCulley, *Keratoconjunctivitis sicca* associated with meibomian secretion polar lipid abnormality, *Archives of Ophthalmology*, volume 116(7), pages 849–52 (1998). Examples of phospholipid compositions for the treatment of dry eye are disclosed in U.S. Pat. No. 4,131,651 (Shah et al.), U.S. Pat. No. 4,370,325 (Packman), U.S. Pat. No. 4,409,205 (Shively), U.S. Pat. No. 4,744,980 and 4,883,658 (Holly), U.S. Pat. No. 4,914,088 (Glonek), U.S. Pat. No. 5,075,104 (Gressel et al.), U.S. Pat. No. 5,278,151 (Korb et al.), U.S. Pat. No. 5,294,607 (Glonek et al.), U.S. Pat. No. 5,371,108 (Korb et al.) and U.S. Pat. No. 5,578,586 (Glonek et al.). U.S. Pat. No. 5,174,988 (Mautone et al.) discloses phospholipid drug delivery systems involving phospholipids, propellants and an active substance.

Another approach involves the provision of lubricating substances in lieu of artificial tears. For example, U.S. Pat. No. 4,818,537 (Guo) discloses the use of a lubricating, liposome-based composition, and U.S. Pat. No. 5,800,807 (Hu et al.) discloses compositions containing glycerin and propylene glycol for treating dry eye.

Although these approaches have met with some success, problems in the treatment of dry eye nevertheless remain. The use of tear substitutes, while temporarily effective, generally requires repeated application over the course of a patient's waking hours. It is not uncommon for a patient to have to apply artificial tear solution ten to twenty times over the course of the day. Such an undertaking is not only cumbersome and time consuming, but is also potentially very expensive. Transient symptoms of dry eye associated with refractive surgery have been reported to last in some cases from six weeks to six months or more following surgery.

Aside from efforts directed primarily to the alleviation of symptoms associated with dry eye, methods and compositions directed to treatment of the dry eye condition have also been pursued. For example, U.S. Pat. No. 5,041,434 (Lubkin) discloses the use of sex steroids, such as conjugated estrogens, to treat dry eye conditions in post-menopausal women; U.S. Pat. No. 5,290,572 (MacKeen) discloses the use of finely divided calcium ion compositions to stimulate pre-ocular tear film production; and U.S. Pat. No. 4,966,773 (Gressel et al.) discloses the use of microfine particles of one or more retinoids for ocular tissue normalization.

Some recent literature reports suggest that patients suffering from dry eye syndrome disproportionately exhibit the hallmarks of excessive inflammation in relevant ocular tissues, such as the lacrimal and meibomian glands. The use of steroids and cytokine release inhibitors to treat dry eye patients has been disclosed: U.S. Pat. No. 5,958,912; Marsh, et al., *Topical nonpreserved methylprednisolone therapy for keratoconjunctivitis sicca in Sjogren syndrome*, *Ophthalmology*, 106(4): 811–816 (1999); Pflugfelder, et. al. U.S. Pat. No. 6,153,607; and Yanni, J. M.; et. al. WO 0003705 A1. Additionally, cyclosporine A [Tauber, *J. Adv. Exp. Med. Biol.* 1998, 438 (Lacrimal Gland, Tear Film, and Dry Eye Syndromes 2), 969] has been disclosed for treating dry eye.

U.S. Pat. No. 5,696,166 discloses the use of certain HETE derivatives, including 15-HETE, for treating drey eye and other disorders requiring the wetting of the eye. According to the '166 patent, the HETE derivatives stimulate mucin production and/or secretion in the conjunctival epithelium and goblet cells following topical ocular application. Jumblatt, et al., *Cornea, vol.* 19, suppl. 2, p. S97 (2000), have recently reported that 15(S)-HETE is an effective secretagogue for the mucin subtype MUC1 and that the inability of 15(S)-HETE to stimulate secretion of the soluble goblet cell mucins (MUC2, MUC5AC) suggests that 15(S)-HETE acts predominantly on non-goblet conjunctival epithelial cells.

SUMMARY OF THE INVENTION

The present invention is directed to methods for the treatment of dry eye and other disorders requiring the wetting of the eye, including symptoms of dry eye associated with refractive surgery such as LASIK surgery. According to the methods of the present invention, inhibitors of acyl-CoA synthetase are administered to a patient suffering from dry eye or other disorders requiring wetting of the eye. The inhibitors of acyl-CoA synthetase are preferably administered topically to the eye.

Among other factors, the present invention is based on the finding that inhibitors of acyl-CoA synthetase stimulate production and/or secretion of the mucin subtype 5AC (MUC5AC), which is known to be derived from goblet cells in human conjunctival tissue.

DETAILED DESCRIPTION OF THE INVENTION

Acyl-CoA synthetase enzymatically converts free fatty acids into acyl-CoA esters which are then used by various acyltransferases to incorporate fatty acids into membrane glycerolipids (such as phospholipids, triglycerides). The synthetase reaction proceeds as follows:

Free fatty acid+CoA+ATP→acyl-CoA+AMP+Ppi

Modulation of the incorporation of fatty acids into membranes can influence the structure and function cells. Inhibitors of acyl-CoA synthetase have been identified by standard biochemical techniques. The triacsins A, B and C are fungal metabolites which are competitive inhibitors of acyl-CoA. All he triacsins are 11-carbon alkenyl chains with an N-hydroxytriazene moiety at the terminus. Triacsin C, 1-hydroxy-3-(E,E,E,E-2'4'6'8'-undecatetraenylidine) triazene, is the most potent of these compounds and is commercially available from Kyowa Medix. Any acyl-CoA synthetase inhibitor is suitable for use in the methods of the present invention, provided it is not toxic.

According to the methods of the present invention, a composition comprising an inhibitor of acyl-CoA synthetase and a pharmaceutically acceptable carrier for topical ophthalmic administration or implantation into the conjunctival sac or anterior chamber of the eye is administered to a mammal in need thereof. The compositions are formulated in accordance with methods known in the art for the particular route of administration desired. The compositions are preferably administered topically to the eye.

The compositions administered according to the present invention comprise a pharmaceutically effective amount of an inhibitor of acyl-CoA synthetase. As used herein, a "pharmaceutically effective amount" is one which is sufficient to reduce or eliminate signs or symptoms of dry eye or other disorders requiring the wetting of the eye. Generally, for compositions intended to be administered topically to the eye in the form of eye drops or eye ointments, the total amount of an inhibitor of acyl-CoA synthetase in the composition will be about 0.001 to 1.0% (w/v).

Preferably, the compositions administered according to the present invention will be formulated as solutions, suspensions and other dosage forms for topical administration. Aqueous solutions are generally preferred, based on ease of formulation, as well as a patient's ability to easily administer such compositions by means of instilling one to two drops of the solutions in the affected eyes. However, the compositions may also be suspensions, viscous or semi-viscous gels, or other types of solid or semi-solid compositions.

The compositions administered according to the present invention may also include various other ingredients, including but not limited to surfactants, tonicity agents, buffers, preservatives, co-solvents and viscosity building agents.

Various tonicity agents may be employed to adjust the tonicity of the composition, preferably to that of natural tears for ophthalmic compositions. For example, sodium chloride, potassium chloride, magnesium chloride, calcium chloride, dextrose and/or mannitol may be added to the composition to approximate physiological tonicity. Such an amount of tonicity agent will vary, depending on the particular agent to be added. In general, however, the compositions will have a tonicity agent in an amount sufficient to cause the final composition to have an ophthalmically acceptable osmolality (generally about 150–450 mOsm, preferably 250–350 mOsm).

An appropriate buffer system (e.g., sodium phosphate, sodium acetate, sodium citrate, sodium borate or boric acid) may be added to the compositions to prevent pH drift under storage conditions. The particular concentration will vary, depending on the agent employed. Preferably, however, the buffer will be chosen to maintain a target pH within the range of pH 6–7.5.

Compositions formulated for the treatment of dry eye-type diseases and disorders may also comprise aqueous carriers designed to provide immediate, short-term relief of dry eye-type conditions. Such carriers can be formulated as a phospholipid carrier or an artificial tears carrier, or mixtures of both. As used herein, "phospholipid carrier" and "artificial tears carrier" refer to aqueous compositions which: (i) comprise one or more phospholipids (in the case of phospholipid carriers) or other compounds, which lubricate, "wet," approximate the consistency of endogenous tears, aid in natural tear build-up, or otherwise provide temporary relief of dry eye symptoms and conditions upon ocular administration; (ii) are safe; and (iii) provide an appropriate delivery vehicle for the topical administration of an inhibitor of acyl-CoA synthetase. Examples of artificial tears compositions useful as artificial tears carriers include, but are not limited to, commercial products, such as Tears Naturale®, Tears Naturalell®, Tears Naturale Free®, and Bion Tears® (Alcon Laboratories, Inc., Fort Worth, Texas). Examples of phospholipid carrier formulations include those disclosed in U.S. Pat. No. 4,804,539 (Guo et al.), U.S. Pat. No. 4,883,658 (Holly), U.S. Pat. No. 4,914,088 (Glonek), U.S. Pat. No. 5,075,104 (Gressel et al.), U.S. Pat. No. 5,278,151 (Korb et al.), U.S. Pat. No. 5,294,607 (Glonek et al.), U.S. Pat. No. 5,371,108 (Korb et al.), U.S. Pat. No. 5,578,586 (Glonek et al.); the foregoing patents are incorporated herein by reference to the extent they disclose phospholipid compositions useful as phospholipid carriers of the present invention.

Other compounds designed to lubricate, "wet," approximate the consistency of endogenous tears, aid in natural tear build-up, or otherwise provide temporary relief of dry eye symptoms and conditions upon ocular administration the eye are known in the art. Such compounds may enhance the viscosity of the composition, and include, but are not limited to:

monomeric polyols, such as, glycerol, propylene glycol, ethylene glycol; polymeric polyols, such as, polyethylene glycol, hydroxypropylmethyl cellulose ("HPMC"), carboxy methylcellulose sodium, hydroxy propylcellulose ("HPC"), dextrans, such as, dextran 70; water soluble proteins, such as gelatin; and vinyl polymers, such as, polyvinyl alcohol, polyvinylpyrrolidone, povidone and carbomers, such as, carbomer 934P, carbomer 941, carbomer 940, carbomer 974P.

Other compounds may also be added to the ophthalmic compositions of the present invention to increase the viscosity of the carrier. Examples of viscosity enhancing agents include, but are not limited to: polysaccharides, such as hyaluronic acid and its salts, chondroitin sulfate and its salts, dextrans, various polymers of the cellulose family; vinyl polymers; and acrylic acid polymers. In general, the phospholipid carrier or artificial tears carrier compositions will exhibit a viscosity of 1 to 400 centipoise ("cps").

Topical ophthalmic products are typically packaged in multidose form. Preservatives are thus required to prevent microbial contamination during use. Suitable preservatives include: benzalkonium chloride, chlorobutanol, benzododecinium bromide, methyl paraben, propyl paraben, phenylethyl alcohol, edetate disodium, sorbic acid, polyquaternium-1, or other agents known to those skilled in the art. Such preservatives are typically employed at a level of from 0.001 to 1.0% w/v. Unit dose compositions of the present invention will be sterile, but typically unpreserved. Such compositions, therefore, generally will not contain preservatives.

The preferred compositions of the present invention are intended for administration to a human patient suffering from dry eye or symptoms of dry eye. Preferably, such compositions will be administered topically. In general, the doses used for the above described purposes will vary, but will be in an effective amount to eliminate or improve dry eye conditions. Generally, 1–2 drops of such compositions will be administered from once to many times per day.

A representative eye drop formulation is provided in Example 1 below.

| Ingredient | Amount (% w/v) |
| --- | --- |
| Triacsin C | 0.001–1.0 |
| Polyoxyl 40 Stearate | 0.1 |
| Boric Acid | 0.25 |
| Sodium Chloride | 0.75 |
| Disodium Edetate | 0.01 |
| Polyquaternium-1 | 0.001 |
| NaOH/HCl | q.s., pH = 7.4 |
| Purified Water | q.s. 100% |

The above composition is prepared by the following method. The batch quantities of boric acid, sodium chloride, disodium edetate, and polyquaternium-1 are weighed and dissolved by stirring in 90% of the batch quantity of purified water. The pH is adjusted to 7.4±0.1 with NaOH and/or HCl. The batch quantity of the inhibitor of acyl-CoA synthetase (preferably as a stock solution) is measured and added. Purified water is added to q.s. to 100%. The mixture is stirred for five minutes to homogenize and then filtered through a sterilizing filter membrane into a sterile recipient.

This invention has been described by reference to certain preferred embodiments; however, it should be understood that it may be embodied in other specific forms or variations thereof without departing from its special or essential characteristics. The embodiments described above are therefore considered to be illustrative in all respects and not restrictive, the scope of the invention being indicated by the appended claims rather than by the foregoing description.

What is claimed is:

1. A method for the treatment of dry eye disorders which comprises administering to a mammal a composition comprising a pharmaceutically acceptable carrier and a pharmaceutically effective amount of an inhibitor of acyl-CoA synthetase.

2. The method of claim 1 wherein the pharmaceutically effective amount of the inhibitor of acyl-CoA synthetase is 0.001–1.0% (w/v).

3. The method of claim 1 wherein the composition is topically administered to the eye.

4. The method of claim 1 wherein the dry eye disorders comprises symptoms of dry eye associated with refractive surgery.

5. The method of claim 1 wherein the inhibitor of acyl-CoA synthetase is triacin C.

6. A method of increasing the production or secretion of mucin subtype 5AC in the eye comprising topically administering to the eye a composition comprising a pharmaceutically acceptable carrier and a pharmaceutically effective amount of an inhibitor of acyl-CoA synthetase.

* * * * *